United States Patent
Wildnauer

(10) Patent No.: US 6,421,120 B1
(45) Date of Patent: Jul. 16, 2002

(54) EXTENDED WAVELENGTH CALIBRATION REFERENCE

(75) Inventor: Kenneth R. Wildnauer, Santa Rosa, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/430,554

(22) Filed: Oct. 29, 1999

(51) Int. Cl.$^7$ .................................................. G01J 1/10
(52) U.S. Cl. ..................................... 356/243.1; 356/450
(58) Field of Search ............................. 356/243.1, 450, 356/519, 454

(56) References Cited

PUBLICATIONS

W. C. Swann, M. A. Hubbard, and S. L. Gilbert—Hybrid Multiple Wavelength Reference Using Fiber Gratings and Molecular Absorption; Bragg Gratings, Photosensitivity, and Poling in Glass Waveguides, OSA Technical Digest (Optical Society of America, Washington DC, 1999), pp. ThE6–1/63, ThE6–2/64 and ThE6–3/65.

*Primary Examiner*—Frank G. Font
*Assistant Examiner*—Andrew H. Lee
(74) *Attorney, Agent, or Firm*—Robert T. Martin

(57) ABSTRACT

Optical wavelength reference apparatus with wide wavelength range. Illuminated by a wideband source, a first reference such as absorption lines in a gas cell is used as a transfer standard, calibrating the response of the secondary reference over the range of the first reference. The performance of the second reference is extrapolated to a wider wavelength range, retaining the stability and accuracy characteristics of the first reference. Suitable secondary devices include etalons such as Fabry-Perot filters and Mach-Zehnder interferometers.

16 Claims, 6 Drawing Sheets

EXTENDED WAVELENGTH CALIBRATION REFERENCE

BACKGROUND OF THE INVENTION

1. Field of the Invention

The present invention pertains to references for calibrating instruments for measuring optical wavelength or frequency, such as optical spectrum analyzers and wavelength meters.

2. Art Background

Devices for measuring the wavelength or frequency of optical signals, such as optical spectrum analyzers or wavelength meters contain a mixture of electronic and mechanical assemblies. Especially with the presence of mechanical assemblies, calibration is an important part of the proper use of these devices. Calibration references provide a set of accurate, known frequencies or wavelengths, either in the form of emission lines, or in the form of absorption lines, that may be used to calibrate instruments.

To be an effective calibration reference, a device must produce these known wavelengths or frequencies with accuracy and stability. One set of references involves using known absorption lines of a gas cell, such as acetylene or methane. When coupled to a wideband light source, such gas cells produce absorption lines which are very stable over environmental changes such as operating temperature, altitude, and humidity. They are also mechanically rugged. Gas cells, while providing physical references, only provide information over a limited frequency or wavelength range. Often times gases to provide references at other wavelengths or frequencies are unavailable, or have undesirable properties, such as degrading over time, or posing handling problems.

Calibration solutions not using gas cells have used expensive technologies which provide calibration not based on physical references. These solutions, such as external cavity lasers, or environmentally compensated etalons, have two main characteristics. First, they are calibrated at the factory during manufacture. Second, they must be designed to have very little change in wavelength over shifts in environmental conditions, or over the trials and travails of transportation, and over time. It is difficult to design such solutions to be stable and yet transportable, and not requiring periodic recalibration against more stable references.

What is needed is an optical calibration reference which is stable, does not require factory recalibration, does not need to be designed to remain constant over environmental change or the effects of time, and provides reference information over a broader band than gas references.

SUMMARY OF THE INVENTION

The calibration reference of the present invention combines a first device, such as a gas cell, which provides a physical reference, with a secondary device which provides predictable variation in amplitude vs. wavelength or frequency. The first device is used as a transfer reference with the secondary device to provide calibration information for that secondary device. The first device is used to calibrate the secondary device over the range of the first device. This information and the response characteristics of the secondary device are then extrapolated to other frequencies or wavelengths of interest outside the range of the first device. One embodiment of the present invention uses gas cell as the first device, and an etalon such as a Fabry-Perot (FP) filter for the second device. Another embodiment of the present invention uses a Mach-Zehnder interferometer as the second device. Another embodiment of the present invention combines the etalon and the gas cell into a single device.

BRIEF DESCRIPTION OF THE DRAWINGS

The present invention is described with respect to particular exemplary embodiments thereof and reference is made to the drawings in which.

DETAILED DESCRIPTION

Stable references are needed in the calibration of optical instruments. To be useful, references need to be accurate and stable, both over the short term and long term.

Absorption lines of gasses provide accurate and stable references. In such a reference, light from a wideband source is passed through a cell containing a gas. The wavelengths of the absorption lines of the gas, such as acetylene or methane, are numerous, and are stable over time and over shifting environmental factors.

In their 1992 paper, "Moderate-Accuracy Wavelength Standards for Optical Communications" printed in "Technical Digest—Symposium on Optical Fiber Measurements, 1992" NIST Special Publication 839 by the United States Department of Commerce, Gilbert et. al identify absorption lines of gasses as providing a reference of suitable stability for calibrating Optical Spectrum Analyzers.

While absorption lines of gasses provide useful references, they cover only a narrow band of wavelengths.

In the present invention, a first reference device, which provides a stable reference, is used as a transfer standard in calibrating a second device, which provides a periodic variation in amplitude over a wider wavelength range. By using the first reference to calibrate the performance of the second, the second device need only provide short-term stability, as its performance is now tied to the performance of the first, more stable, device. While the example of a gas cell providing absorption lines is used in the preferred embodiments as a first reference, it is understood that any reference having the needed stability could be so used.

Figure 1:
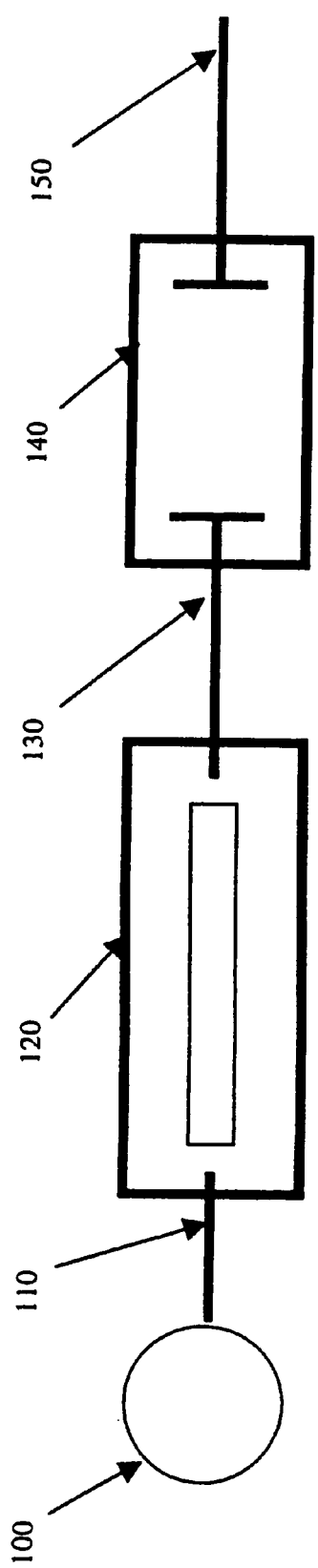
FIG. 1 shows a first embodiment of the invention.

In a first embodiment of the invention, as shown in FIG. 1, wideband light source 100 is coupled to fiber 110 which passes the light through gas cell 120. Fiber 130 couples this light, which now contains absorption lines from gas cell 120, to etalon 140. The output of etalon 140 is coupled to fiber 150, and to the device to be calibrated.

Light source 100 may be any wideband source, such as a white light source, a light emitting diode (LED), an edge-emitting light emitting diode (EELED), an amplified spontaneous emission (ASE), or a tunable laser. It can also be two or more sources, where at least one of the sources has a wavelength range which covers the wavelength overlap of the first and second devices. The remaining source(s) are then used to cover the extended wavelength range provided by the second device. Gas cell 120 provides absorption lines in a particular part of the spectrum, overlapping at least a portion of the periodic response of etalon 140. Suitable gasses include acetylene, which has useful absorption lines in the 1.5 micrometer region, methane, hydrogen cyanide, carbon monoxide, hydrogen iodide, and water vapor.

Etalon 140 provides a periodic amplitude versus wavelength response over a wide wavelength range. An example of a suitable etalon is a Fabry-Perot etalon. Such an etalon consists of two reflective surfaces with a transmission medium between them. The etalon produces a periodic amplitude versus wavelength response determined by the physical path length between its surfaces, and the index of refraction of the medium between them. The free spectral range (FSR) is determined by the optical path length between the reflective optical surfaces of the cavity. If the optical medium of the cavity is not a vacuum, the dispersion of the cavity medium must be known. The finesse is determined by the reflectivity of the optical surfaces. Both the FSR and the finesse together determine the bandwidth or selectivity of the individual transmission peaks. Fabry-Perot etalons give sharp transmission peaks when the finesse of the device is high. Etalons may also be fabricated from bulk optic devices, dielectric stacks, and fiber optics, etc.

In the embodiment of FIG. 1, wideband source 100 illuminates fiber 110 producing a first set of stable absorption lines introduced by gas cell 120, present on fiber 130. A set of transmission lines are introduced by etalon 140, and this spectrum containing both sets of lines is present on fiber 150.

By examining first the known absorption lines introduced by gas cell 120, the spacing characteristics of the additional lines introduced by etalon 140 are calculated over the range covered by gas cell 120. Once the characteristics of etalon 140 are known over this wavelength range, they can be extended over its wider range, thereby providing accurate references over this wider range, and transferring the accuracy of the first reference, a gas cell in the present embodiment, to the etalon.

Etalon 140 may be either fixed or tunable. Etalons are made tunable by varying the spacing between the optical elements, changing the refractive index of the medium between them, or a combination of these approaches. Temperature tuning, usually by mounting heating/cooling elements on the etalon and controlling these temperature control elements through a control loop, operates usually to both change the refractive index of the optical medium, if the medium is not a vacuum, as well as changing the physical path length through thermal expansion of the materials used to separate or enclose the optical surfaces. Voltage tuning and piezoelectric tuning approaches are also used. Temperature control, where the etalon is held at a constant temperature, is also useful in stabilizing the performance of the etalon, holding it to a controlled temperature.

Tuning of the etalon can simplify the determination of the free spectral range (FSR), at presumably an increase in cost. This is done by being able to tune the device so that more than one transmission maximum falls precisely on gas cell absorption minima (reference lines of the first device), and thus the spacing between these transmission maxima (reference lines of the second device) are easily determined. It should also be noted that the idea of tuning can be applied to other devices which exhibit a changing transmission function which may be used as the second reference device.

Standard digital signal processing techniques are used to calibrate the second reference device when the reference lines from the second device do not precisely coincide in frequency or wavelength with reference lines of the first device. This can be done in several ways. The easiest is to use the first reference device to calibrate the instrument over the wavelength or frequency range of the first reference device. The instrument is then used to measure the second reference device over this same wavelength or frequency range. This would lead to a degree of accuracy determined by the particulars of the errors associated with the instrument that is calibrated. An embodiment similar to FIG. 3 would facilitate such a method. A more sophisticated method is one where the multiplication of the transfer functions of the reference devices are understood for varying relative offsets between the reference lines of the two reference devices. Further this information can be stored in the instrument that is to be calibrated or it can be calculated with each calibration line measurement of interest.

Figure 2:
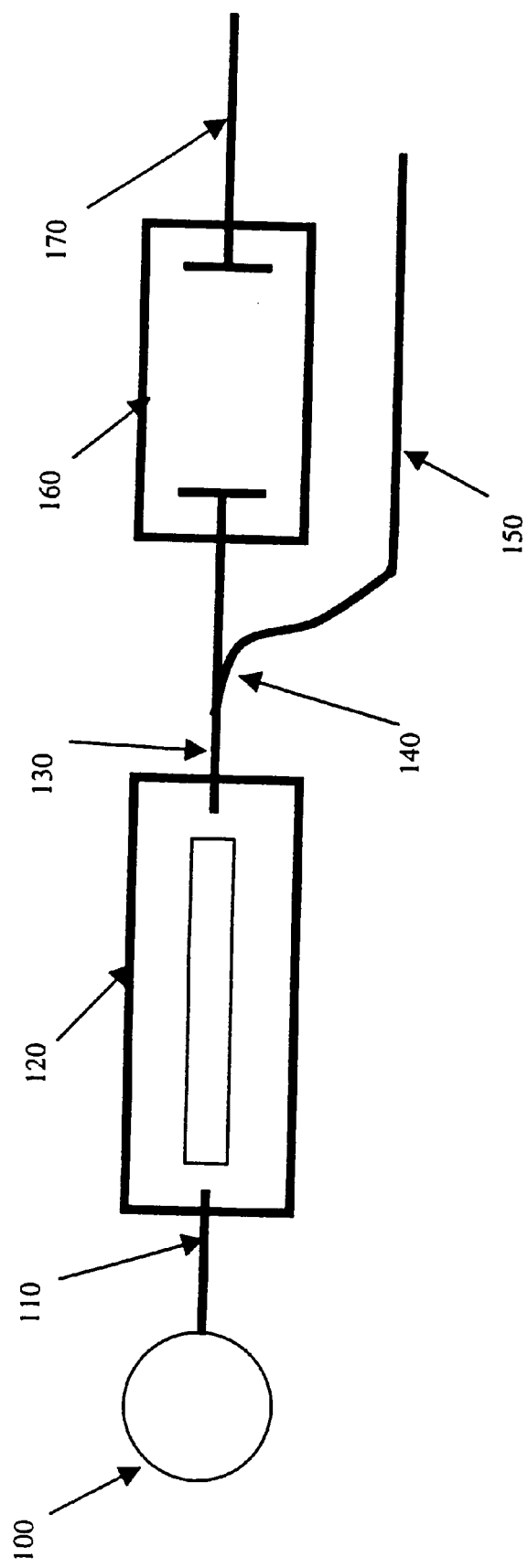
FIG. 2 shows a second embodiment of the invention.

FIG. 2 shows a second embodiment of the present invention. In this embodiment, wideband source 100 illuminates fiber 110 and gas call 120. The output of gas cell 120 is sent to coupler 140, which provides input to etalon 160 as well as an output 150 containing only the absorption lines of gas cell 120. By switching between the output of gas cell 120 and the combined outputs of gas cell 120 and etalon 160, it may be easier to identify absorption lines where they overlap. Coupler 140 could be replaced by a switch.

Figure 3:
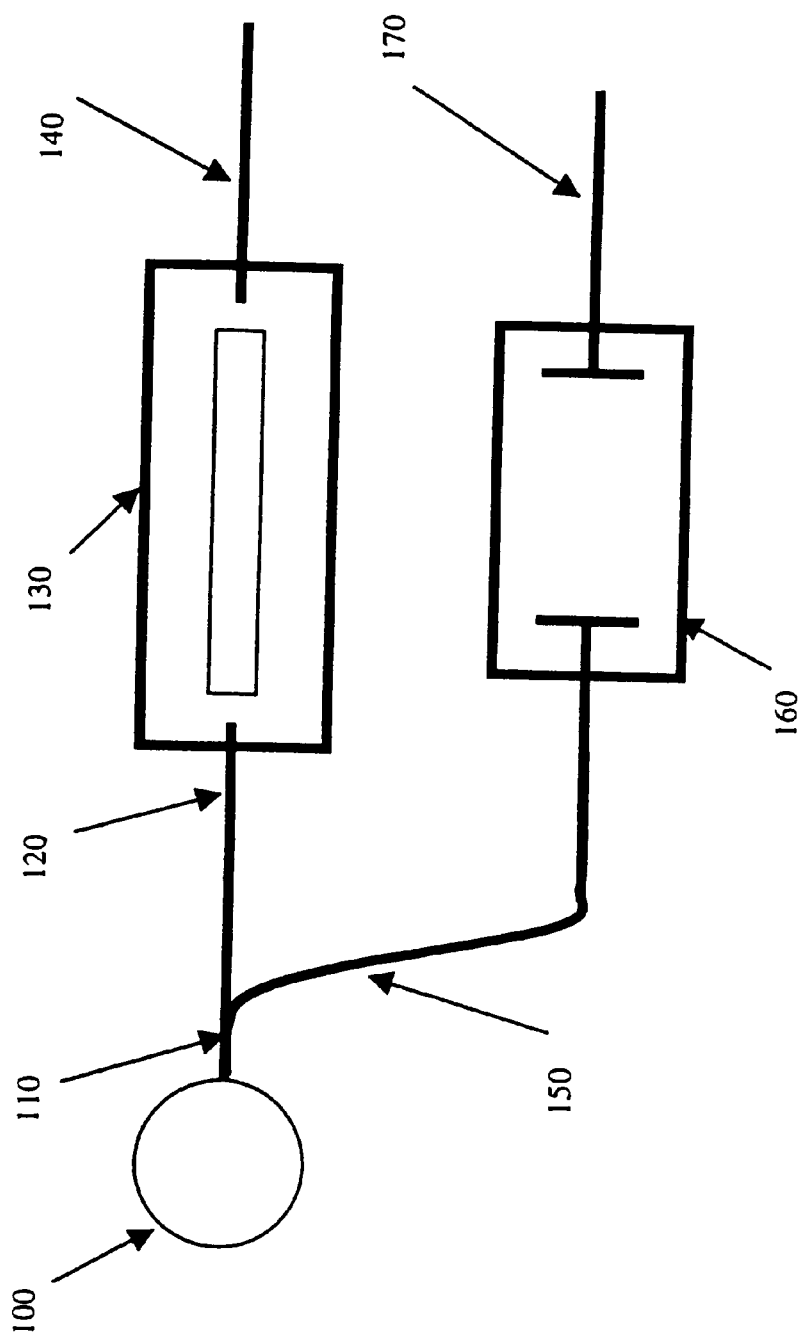
FIG. 3 shows a third embodiment of the invention

FIG. 3 shows an alternative embodiment in which the output of wideband source 100 is split by coupler 110, feeding fiber and gas cell 130. Fiber 140 presents just the absorption spectrum of gas cell 130. The other output of coupler 110 through fiber 150 feeds etalon 160, presenting the transmission spectrum on fiber 170. This embodiment requires the instrument being calibrated switch between the signals present on fibers 140 and 170. Coupler 110 could be replaced by a switch.

Figure 4:
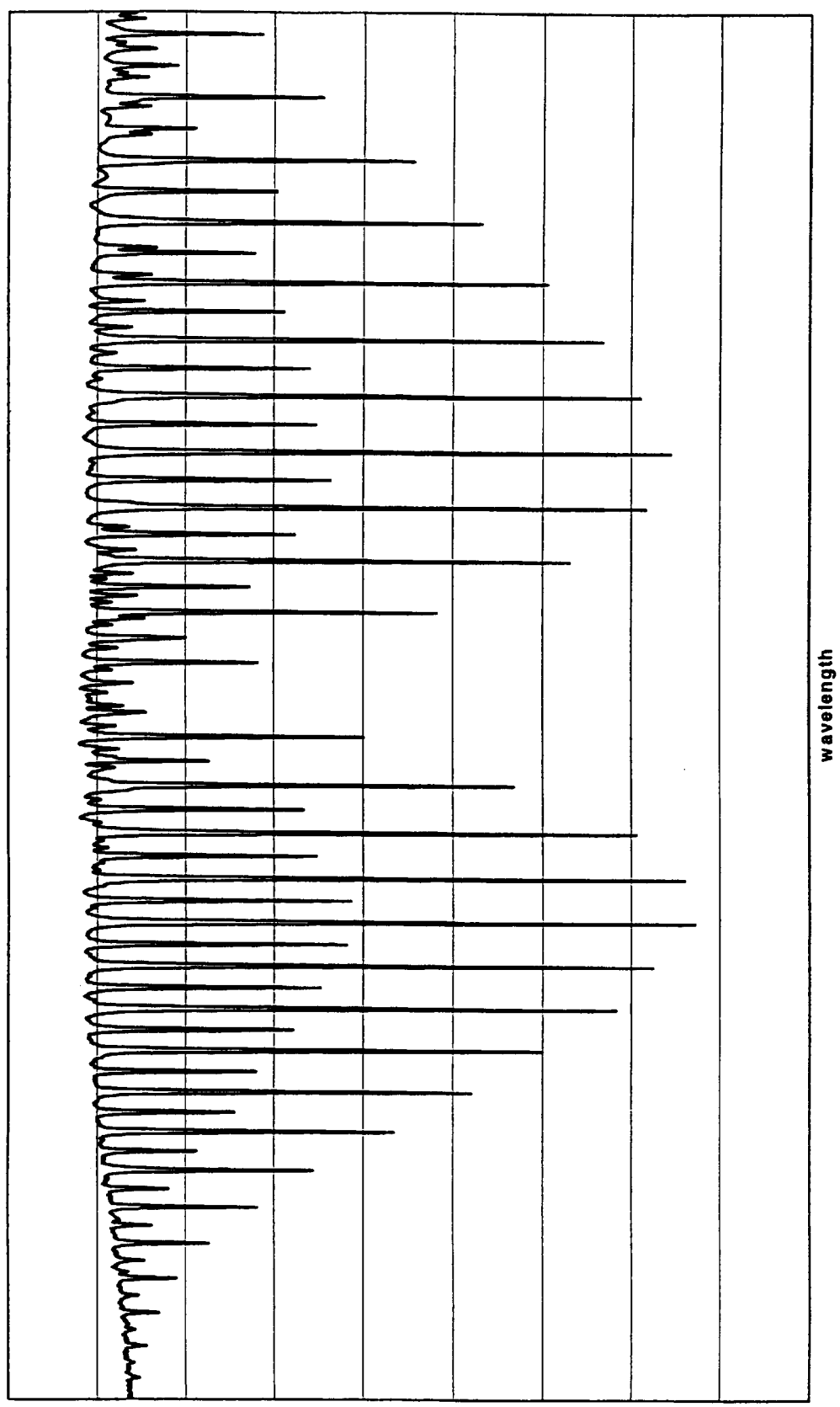
FIG. 4 shows the spectral response of a gas cell.
Figure 5:
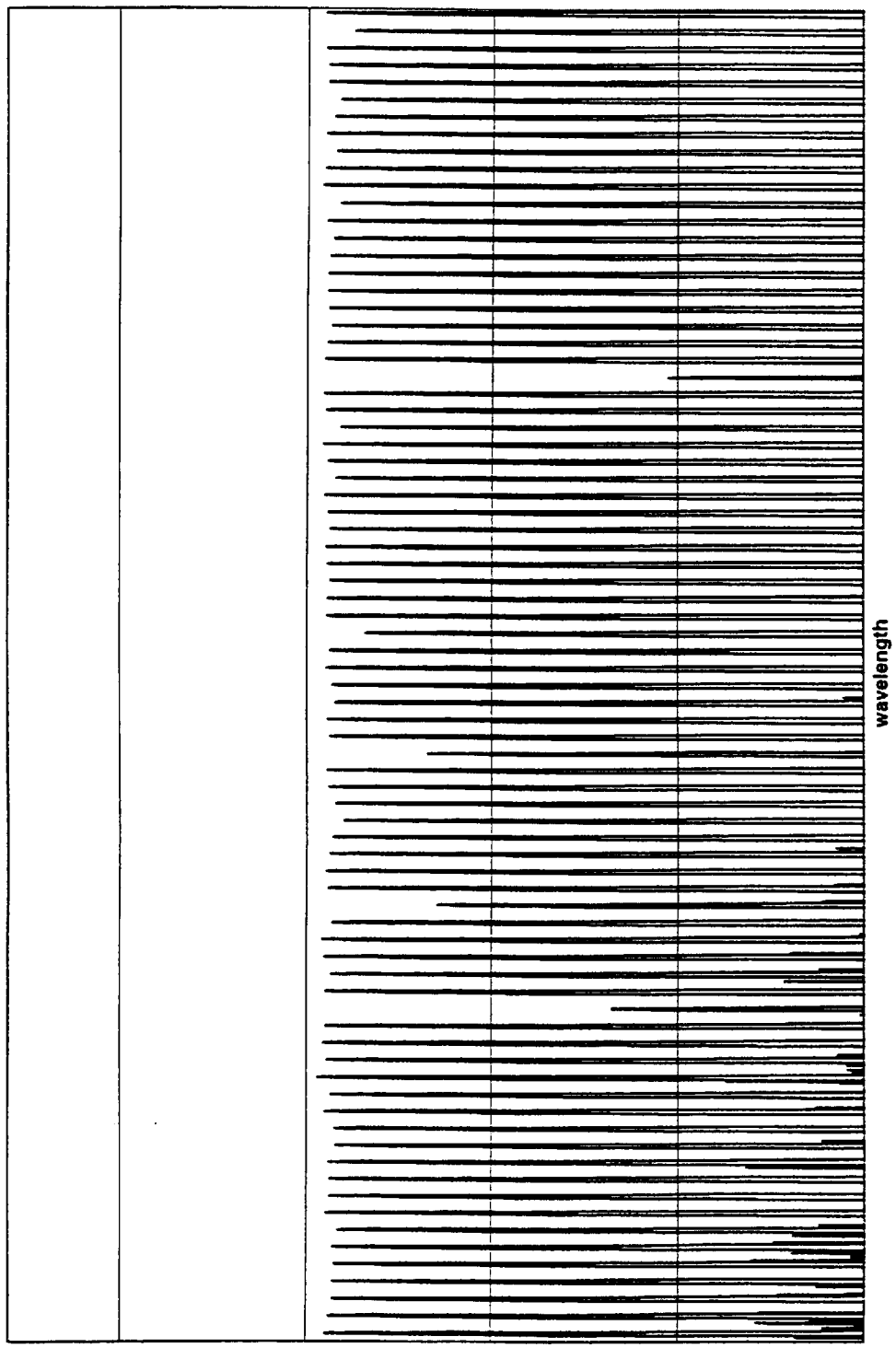
FIG. 5 shows the combined spectral response of a gas cell and an etalon.

FIG. 4 shows the characteristic absorption line spectrum of a gas cell, present on port 150 of FIG. 2. FIG. 5 shows this spectrum combined with the transmission spectrum of etalon 160 of FIG. 2, the output present on port 170. Most prevalent in FIG. 5 are the characteristic sharp transmission peaks of a high finesse etalon. Where these transmission peaks coincide with absorption lines from the gas cell, the amplitude of the peaks are clearly reduced.

Other devices may be used as the secondary reference, as long as they have a predictable and periodic amplitude—wavelength response. Another suitable device for use as a secondary reference is the Mach-Zender interferometer. The response of the Mach-Zehnder interferometer is more sinusiodal, but may be processed to give sharp dips.

Figure 6:
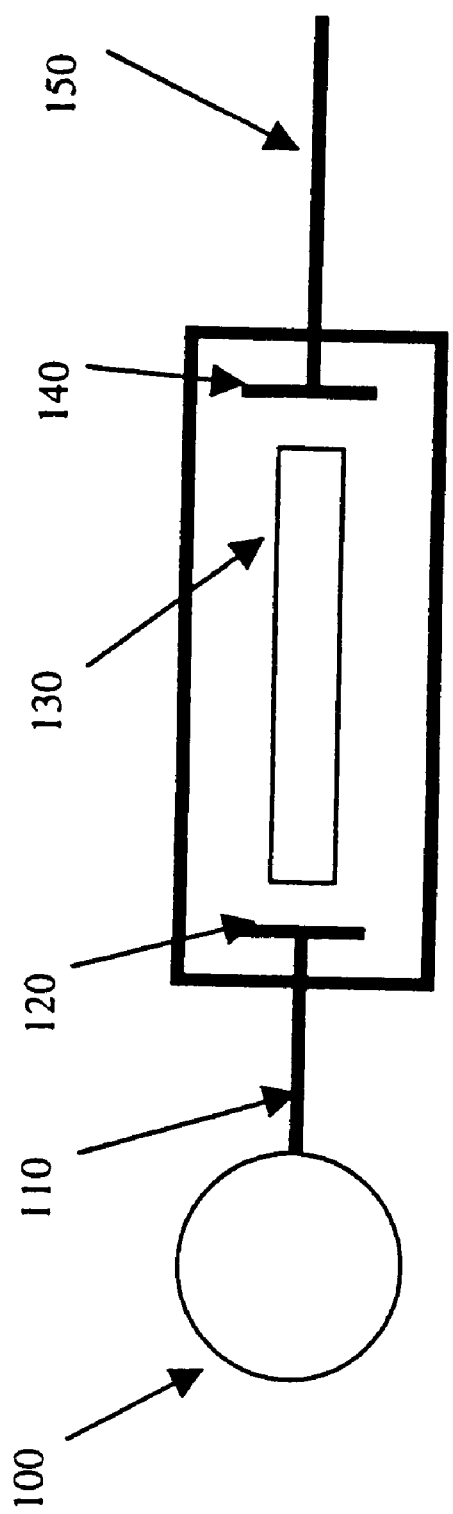
FIG. 6 shows a fourth embodiment of the invention.

The embodiment of FIG. 6 takes advantage of the physical construction of the etalon to fold in the function of the gas absorption cell. Wide band source 100 illuminates fiber 110, and first etalon surface 120. Etalon cavity 130 is filled with the reference gas. Light passing through second etalon surface 140 is coupled to fiber 150. The presence of the gas in etalon cavity 130 produces absorption lines known for the gas over a narrow wavelength range. The etalon itself produces periodic transmission lines over a broader range. The gas may also be present in a cell placed between partially reflective surfaces 120 and 140. These surfaces may or may not form part of the actual gas cell. The performance of this combined device is characterized by the finesse and spacing of the reflective surfaces, and the pressure of the gas between them. These parameters are varied to achieve the desired free spectral response and absorption depth. In the preferred embodiment, gasses such as methane, acetylene, hydrogen cyanide, hydrogen iodide, carbon monoxide, or water vapor may be used. Gasses may be combined, and the cell may also contain a nonreactive gas used as a filler. For example, a gas cell may combine methane and acetylene, or acetylene and a filler such as argon or nitrogen.

The foregoing detailed description of the present invention is provided for the purpose of illustration and is not intended to be exhaustive or to limit the invention to the precise embodiments disclosed. Accordingly the scope of the present invention is defined by the appended claims.

What is claimed is:

1. A wide band optical reference, comprising:

a wideband light source, a first reference coupled to the wideband light source, producing a first set of reference lines at predetermined stable frequencies or wavelengths, and a second reference coupled to the output of the first reference, producing a second set of reference lines over a wider wavelength range than the first reference, the wavelength range of the second reference at least partially overlapping the wavelength range of the first reference.

2. The wideband optical reference of claim 1 where the first reference is a gas cell.

3. The wideband optical reference of claim 2 where the gas cell further comprises a gas cell containing one or more of: methane, acetylene, hydrogen cyanide, hydrogen iodide, carbon monoxide, or water vapor.

4. The wideband optical reference of claim 3 where the gas cell may also contain a nonreactive gas.

5. The wideband optical reference of claim 2 where the second reference is tunable.

6. The wideband optical reference of claim 2 where the second reference is an etalon.

7. The wideband optical reference of claim 6 where the etalon is tunable.

8. The wideband optical reference of claim 2 where the second reference is a Mach-Zehnder interferometer.

9. A method of providing a wideband optical reference, comprising the steps of:

illuminating a first reference with a wideband source, the first reference producing a first set of reference lines at predetermined stable frequencies or wavelengths, coupling the output of the first reference to a second reference producing a second set of reference lines over a wider wavelength range than the first reference, the wavelength range of the second reference at least partially overlapping the wavelength of the first reference, using the first set of reference lines to characterize the second set of reference lines produced by the second reference over the region covered by the first reference, and extrapolating the characterization of the second reference to a wavelength range outside the range of the first reference.

10. The method of claim 9 where the step of illuminating a first reference further comprises illuminating a gas cell.

11. The method of claim 9 where the second reference further comprises an etalon.

12. The method of claim 9 where the second reference further comprises a Mach-Zehnder interferometer.

13. A method of providing a wideband optical reference, comprising the steps of:

illuminating a first reference with a wideband source, the first reference producing a first set of reference lines at predetermined stable frequencies or wavelengths, coupling or switching the output of the first reference to a second tunable reference producing a second set of reference lines over a wider wavelength range than the first reference, the wavelength range of the second reference at least partially overlapping the wavelength of the first reference, tuning the second reference so that at least one reference line of the first reference and one line of the second reference precisely or substantially overlap, using the first set of reference lines to characterize the second set of reference lines produced by the second reference over the region covered by the first reference, and extrapolating the characterization of the second reference to a wavelength range outside the range of the first reference.

14. The method of claim 13 where the step of illuminating a first reference further comprises illuminating a gas cell.

15. The method of claim 13 where the second reference further comprises a tunable etalon.

16. The method of claim 13 where the second reference further comprises a tunable Mach-Zehnder interferometer.

* * * * *